United States Patent [19]
Thatcher

[11] 3,959,905
[45] June 1, 1976

[54] APPARATUS FOR MOUNTING TAPE CONTAINING RECORDED INFORMATION

[76] Inventor: Arthur K. Thatcher, Box 392, Merritt Island, Fla. 32952

[22] Filed: Jan. 22, 1975

[21] Appl. No.: 543,122

Related U.S. Application Data

[62] Division of Ser. No. 462,500, April 4, 1974, which is a division of Ser. No. 348,749, April 6, 1973, abandoned.

[52] U.S. Cl. ................................................ 40/124
[51] Int. Cl.² ........................................ G09F 1/00
[58] Field of Search .............. 40/152, 152.1, 158 R, 40/124, 124.4, 106.1; 269/47, 53, 54.4, 54.5

[56] References Cited
UNITED STATES PATENTS

| | | | |
|---|---|---|---|
| 3,067,666 | 12/1962 | Coffman | 40/106.1 X |
| 3,635,558 | 1/1972 | LePeer et al. | 40/152 X |
| 3,650,057 | 3/1972 | Johnson et al. | 40/158 R |

*Primary Examiner*—Russell R. Kinsey
*Assistant Examiner*—John H. Wolff
*Attorney, Agent, or Firm*—Daniel W. Sixbey; Charles M. Leedom; E. Barron Batchelder

[57] ABSTRACT

Method and apparatus is disclosed for editing and mounting segments of recording tape containing prerecorded visual information, such as segments of an electrocardiogram (ECG) recording tape. The disclosed apparatus includes an editor for storing and feeding the tape past a window through which the tape may be viewed. Upon detection of a desired tape segment, the tape is halted and marked with the aid of a scale mounted adjacent the window opening. Thereafter, the tape is severed at each mark to form a segment having a longitudinal length corresponding to the particular type of information contained on the severed tape segment. In the preferred embodiment, the apparatus is adapted to process electrocardiogrphic recording tape and the editor scale includes a zero mark and a plurality of index marks spaced from the zero mark by distances corresponding to the desired longitudinal length of various groups of lead segments such as ECG leads I–III, $V_1$–$V_6$, aVR, aVL and aVF. The method includes mounting the lead segments in a predetermined overlapped sequence in order to display al standard ECG lead segments within an area of 8½ by 8½ inches on a standardized lead segment mounting chart. To assist in alignment of the various lead segments, corresponding alignment holes may be formed in both the lead segments and mounting chart. A base having a plurality of upright pegs is provided to receive the mounting chart and punched segments in a predetermined arrangement.

7 Claims, 8 Drawing Figures

APPARATUS FOR MOUNTING TAPE CONTAINING RECORDED INFORMATION

This is a division of application Ser. No. 462,500 filed Apr. 4, 1974 which is a division of application Ser. No. 348,749 filed Apr. 6, 1973, now abandoned.

BACKGROUND OF THE INVENTION

1. Field of the Invention

This invention relates to a method and apparatus for editing and mounting visual information recorded on tape.

2. Description of the Prior Art

It is commonplace in many fields of technology to record information, such as electrocardiographic information, in a visual form on standardized elongated strips of tape. The amount of recorded data is often far in excess of that which is necessary or pertinent for immediate analysis and/or for storage and future reference. This problem is ordinarily solved by visually inspecting the tape for selection of representative segments which are removed with scissors for mounting on a mounting chart, thereby forming a composite record of the selected information.

Modern electrocardiographs are generally capable of producing 12 standardized leads proportional to potentials measured by electrodes placed at selected locations on the patient's body. These lead signals include:

Lead I - difference of potential between the left arm and the right arm

Lead II - difference of potential between the left leg and the right arm

Lead III - difference of potential between the left leg and the left arm

Lead aVR - augmented difference in potential between the right arm and the left arm and leg electrically connected together Lead aVL - augmented difference in potential between the left arm and the right arm and left leg electrically connected together Lead aVF - augmented difference in potential between the left leg and the left and right arms electrically connected together Leads $V_1$ through $V_6$ - potential measurements, taken at predetermined chest locations of the patient.

An unedited ECG tape includes successive sections containing visually recorded information such as a line tracing for each of the above 12 leads. Numerous attempts have been made to provide an efficient editor for facilitating selection and removal of sample segments representative of each lead and for providing a standardized mounting chart for displaying and storing the selected segments. For example, U.S. Pat. No. 3,261,250 to Littmann discloses an ECG lead segment cutting device including a rectangular cutting blade adapted to remove segments of constant uniform size. Furthermore, U.S. Pat. No. 3,382,127 to Littmann et al discloses a method for mounting ECG lead segments of uniform size on a standardized chart including a frame adapted to facilitate alignment of the lead segments with preselected areas on the chart.

While the disclosed Littmann system is well suited for the purpose intended, an ideal ECG mounting system would permit all 12 lead segments recorded on standard 2½ inch wide ECG tape to be displayed on one side of a standard chart (8½ by 11 inches) with sufficient space left for patient data and comments. Obviously, the Littmann chart cannot provide these characteristics since the entire chart surface is used to display 12 leads. In the ideal system, each of the lead segments must be sufficiently long to display all of the required information. This length differs with the type of lead in question. For example, at least one lead, preferably lead II, should be long enough to permit identification of the auricular complex and accurately determine the pulse rate. Accordingly, lead II should be approximately 6 inches of standard ECG tape. The remaining leads may be considerably shorter. Accordingly, a simplified ECG tape editor system is needed for facilitating division of a standard ECG tape into selected segments of varying predetermined lengths, depending upon the type of information contained thereon. At the same time, the system should be adaptable to a variety of tape widths while facilitating accurate marking of desired tape segments for subsequent cutting into predetermined lengths required by the particular chart on which the segments are to be mounted.

Tape editing devices are, of course, notoriously well known for a variety of specific applications. For example, note U.S. Pat. No. 1,044,258 to Schaffer issued Nov. 12, 1912, which discloses a device for mending film including a film clamp, cutter and gauge mounted on a single base. No tape editor, however, has been disclosed which permits viewing of the tape for selection of desired segments and for marking of the ends of the selected segments in varying lengths depending upon the information contained on the segments.

SUMMARY OF THE INVENTION

The primary purpose of this invention is to provide both method and apparatus for accurately and easily editing tape containing visual information to form segments of predetermined sizes. To realize this purpose, apparatus is provided by which unedited tape is viewed and marked with the aid of a scale to permit accurate removal of selected segments having predetermined lengths corresponding to the information contained on the tape.

Another purpose of this invention is to provide apparatus for editing a tape containing prerecorded visual information by selecting and removing information segments each of which has one of a plurality of predetermined lengths corresponding to the particular type of information contained on the segment. The apparatus includes a base for storing the tape for longitudinal advance over a top portion of the base. Guide means are provided for guiding the tape including a cover element having a window through which the information contained on the tape may be viewed. Mounted adjacent one edge of the window is a scale for permitting a selected segment of the tape to be accurately marked at end points separated by a predetermined distance corresponding to the type of information contained on the segment. After being marked, the tape may be severed at each mark location to form tape segments of predetermined length.

Still another object of this invention is to insure alignment of the removed segments by providing means for punching accurately positioned alignment holes in each information segment. In one embodiment the punch means includes a base and pivoted upper portion mounted on the base for translational movement between predetermined locations corresponding to the scale index marks.

A more specific object of the method of this invention is to form electrocardiogram lead segments having predetermined lengths for mounting on a standardized chart (8½ by 11 inches) in a manner designed to display the maximum amount of information in the minimum amount of space.

A further object of the method of this invention is to provide steps by which the 12 standard ECG lead segments may be mounted on a standardized chart (8½ by 11 inches) by overlapping the upper margin of selected lead segments with other lead segments or by removing the upper margin entirely. This objective is obtained, however, without reducing the total amount of information ordinarily displayed on a standard ECG chart.

DESCRIPTION OF THE PREFERRED EMBODIMENTS

Figure 1:
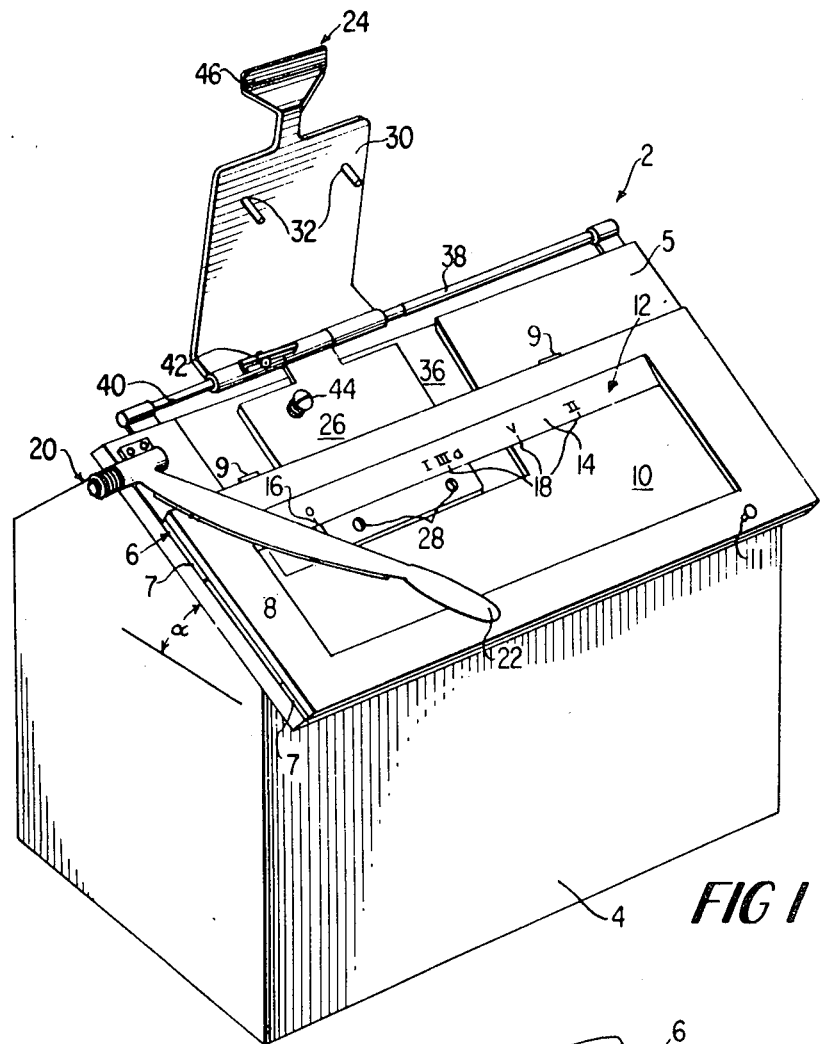
FIG. 1 is a perspective view of an apparatus for editing electrocardiogram tape in accordance with one embodiment of this invention.

Reference is made to FIG. 1 wherein an apparatus 2 for editing tape such as standard electrocardiogram tape is illustrated including a base 4 having a removable upper plate 5 on which is mounted a guide means 6 for guiding tape over the upper plate. The guide means 6 includes a pair of elongated bars 7 mounted on plate 5 along the longitudinal edges of the tape and a cover element 8 containing a window 10 through which the information recorded on the tape may be viewed as the tape is advanced by hand or by mechanical drive (not shown) over the upper portion of the base.

Cover element 8 is mounted by hinges to one elongated bar 7 by a pair of hinges 9, whereby the cover element may be lifted by means of handle 11 for initial feeding of the end portion of an unedited tape into guide means 6. Upon rotation of the cover element into the normal position bridging bars 7, the tape is secured within the guide means and may be viewed and marked through window 10 of cover element 8. In order to facilitate viewing of the unedited tape through window 10, the upper plate 5 of the base is arranged at an angle $\alpha$ between 30 and 45° with respect to the horizontal. Gauge means 12 are provided for permitting a selected segment of the tape to be accurately marked at end points separated by a predetermined distance corresponding to the type of information contained on the selected segment. Such marking may occur while the selected information segment is positioned within window 10 of the guide means cover element 8. Gauge means 12 includes a scale 14 adjacent one edge of the window parallel to the longitudinal axis of the tape. As indicated in FIG. 1, scale 14 may have a zero mark 16 and a plurality of index marks 18 spaced from the zero mark by distances corresponding to the abovementioned predetermined length, respectively. Window 10 within cover element 8 is rectangular and one edge of the cover element adjacent a longitudinal edge of the tape is sloped toward the tape to form a scale mounting surface immediately adjacent the tape, whereby the index markings on scale 14 are brought immediately adjacent the longitudinal edge of the tape segment to be marked. Errors due to parallax are thereby substantially eliminated. At one end of the cover element 8, adjacent the point of exit of the tape being edited, severing means 20 are provided for cutting the tape perpendicularly to the longitudinal axis of the tape. While in FIG. 1 the tape editor is adapted for movement of tape from right to left, it is of course possible to design the tape editor for movement of tape in the opposite direction, depending on whether the operator is left or right handed. When a tape segment is marked while contained within the cover window, the marked segments may be advanced to the severing means which in FIG. 1 is illustrated as a pivoted bar cutting element 22. By employing a bar cutting element, the tape segment may be severed with extreme accuracy to form an information segment of predetermined length corresponding to the information contained on the segment.

As will be explained more completely below, selected lead segments, such as ECG lead segments, often necessitate accurate alignment on a standardized chart in such a manner as to minimize the amount of space required for display of the information contained thereon. To assist in this alignment process, punch means 24 are provided for punching at least one alignment hole in a selected segment of tape when the segment is positioned within the cover element window 10. The punch means includes a base element 26 containing a pair of apertures 28 and an upper portion 30 pivotally mounted to the base portion and having a pair of punches 32 positioned to project through the upper surface of the tape into the apertures of the base portion as the upper portion is rotated toward the base portion. As illustrated in FIG. 1, the upper plate 5 of base 4 includes a recess 36 for permitting the base element of the punch means to be translated along the longitudinal path of the tape to preselected positions corresponding to the desired location of the alignment holes in the information segment being punched. In other words, the punch means is translatable to preselected positions wherein the punch means may be used to punch holes in the tape segments in accordance with the location of corresponding alignment holes on a standardized mounting chart. The accurate positioning of these alignment holes permits the use of a specially designed alignment base to be explained more fully below. The base element 26 and upper portion 30 are mounted for longitudinal movement along a rod element 38 connected with the upper plate 5. A plurality of indentations 40 are provided along rod 38 to receive a spring biased detent 42 adapted to retain the punch means in a preselected position along rod 38. Base element 26 and upper portion 30 are biased apart by a spring element 44; the punch means being operable by depression of handle 46 to force punches 32 through the tape segment and into apertures 28. Of course if the alignment peg board is specially designed, the required holes may be arranged so as not to require translation of the punch means.

Figure 2:
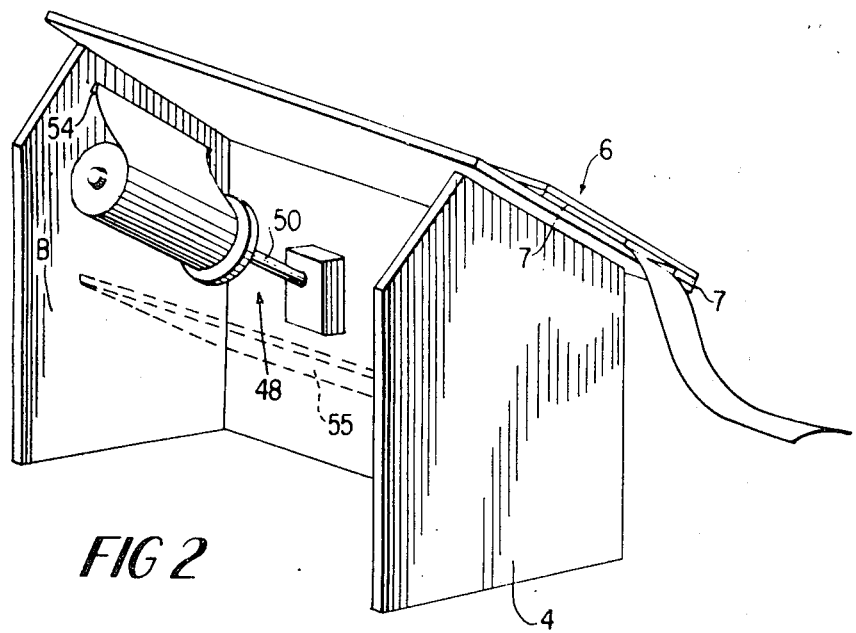
FIG. 2 is a perspective view of the apparatus disclosed in FIG. 1 taken from the back side and disclosing means for storing unedited tape.

As illustrated more clearly in FIG. 2, the base 4 includes storage means 48 having a peg 50 connected with base 4 around which a role of unedited tape may be rotatably mounted. By arranging peg 50 at an angle $\beta$ equal in magnitude to the orientation of the upper plate 5, the tape may be unrolled and advanced through slot 54 contained in one side of the base into the guide means 6 mounted on upper plate 5. A shelf 55, illustrated in dotted lines, may be included to provide additional storage means for storing a roll of tape.

Figure 3:
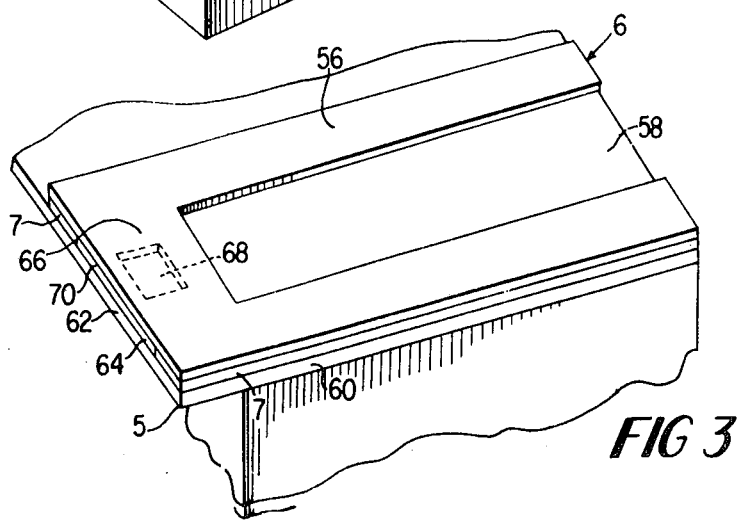
FIG. 3 is a perspective view partially cut away of a cover element for holding the tape in the upper portion of the editing apparatus in accordance with another embodiment of this invention.

FIG. 3 illustrates a modification of the cover element illustrated in FIG. 2 in that the guide means 6 includes a cover element 56 which is U-shaped and is secured to the upper plate 60 of the base 4 to permit the tape to enter the guide means 6 through the open portion 58 of the U-shaped cover element 56, thereby facilitating initial feeding of the tape into the guide means. The upper plate 60 of base 4 includes a laterally extending portion 62 at one side of the base and U-shaped cover element 56 is mounted on bars 7 to form an exit slot 64 for the tape between the interconnecting portion 66 of the U-shaped cover element 56 and the upper plate extension 62. To permit manual positioning of the tape within the exit slot 64, the upper plate extension 62 contains an opening 68 immediately below the interconnecting portion 66 of the U-shaped cover 56 which opening is sufficiently large to permit insertion of an operator's finger for engagement with the under surface of the tape. The lower edge 70 of the interconnecting portion 66 or the upper edge of extension 62 immediately adjacent slot 64 may be sharpened in order to provide a cutting edge against which the tape may be severed, thereby eliminating the need for a bar cutting element. Both cover element 8 illustrated in FIG. 1 and cover element 56 illustrated in FIG. 3 may be formed of transparent material to further facilitate feeding and positioning of the tape within the guide means.

Figure 4:
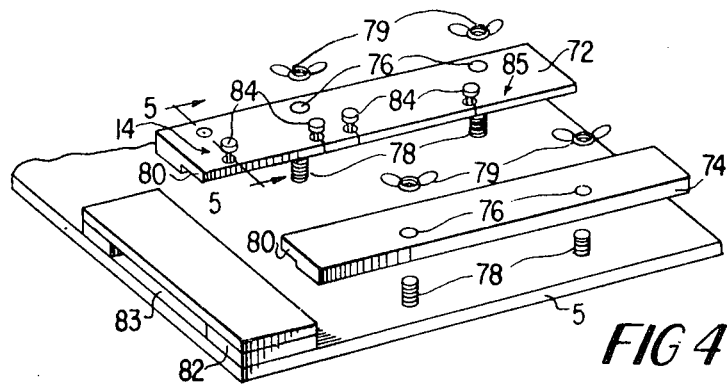
FIG. 4 is an exploded perspective view of yet another modified form of the cover element in accordance with this invention.
Figure 5:
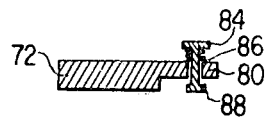
FIG. 5 is a cross-sectional view of one portion of the cover element illustrated in FIG. 4 taken along lines 5—5.

Referring now to FIG. 4, a further embodiment of the guide means is disclosed wherein the cover element includes a pair of removable elongated bars 72, 74 secured by wing nuts 79 to a pair of upstanding threaded studs 78 mounted on upper plate 5 and received in apertures 76 of the elongated bars. Bars 72, 74 are positioned along each longitudinal edge of the tape and extend inwardly toward the longitudinal edges, respectively, for a distance sufficient to define a channel having a width equal at least to the width of the tape. Different sized tape may be accommodated by changing the widths of the bars 72, 74 or by forming transverse slots either in plate 5 or in bars 72 and 74 for receiving studs, thereby permitting transverse adjustment within a predetermined range. Each bar includes an upper lip 80 extending over the associated longitudinal edge of the tape. Upper lips 80 secure the tape within the guide means and at the same time permit the tape to be viewed and marked in the space therebetween. The guide means, as illustrated in FIG. 4, also include a permanently attached element 82 for forming an exit slot 83 through which the tape passes out of the editor. In order to more easily mark the end points of a selected tape segment, a plurality of markers 84 are mounted for longitudinal movement within a lip 80 of one bar 72. Each marker 84 is aligned with one index supporting the tape scale 14. Each marker 84 passes through one of the marks on the scale. Accordingly, markers 84 are spaced by a distance equal to the predetermined length associated with information recorded on tape. As illustrated more clearly in FIG. 5, each marker 84 is spring biased away from the upper surface of the tape by a spring element 86. To mark the tape in the desired location, marker 84 merely needs to be depressed into engagement with the tape margin to form a depression in the tape or to impart a marking substance contained on an end 88 of the marker. Disposable punches could also be mounted in this fashion.

Figure 6:
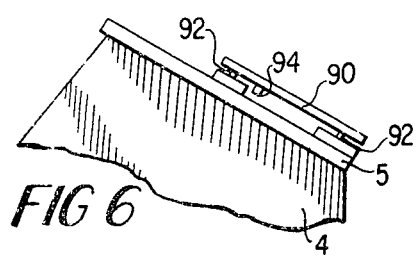
FIG. 6 is a side elevational view of a cover element arranged in accordance with still another embodiment of the subject invention wherein the cover element is mounted for translational motion with respect to the base of the editing apparatus.

With reference to FIG. 6, yet another embodiment of the guide means constructed in accordance with this invention is disclosed wherein a cover element 90 is mounted for translational movement toward and away from the upper surface of an information tape contained within the guide means. Cover element 90 may be supported on pins 92 and normally spring biased in the upper direction by spring elements (not illustrated). One or more punch elements 94 may be mounted in depending fashion from cover element 90 in alignment with corresponding apertures contained in the upper plate 5, whereby alignment apertures may be formed in a selected tape segment by depression of the cover element 90.

Figure 7:
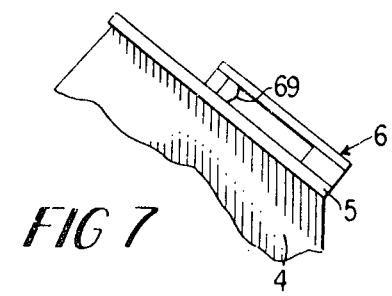
FIG. 7 is a side elevational view of the editor apparatus in accordance with this invention illustrating a cutter element for removing the upper margin of an information tape.

FIG. 7 illustrates a cutter element 96 positioned within the exit slot of a guide means 6 in accordance with this invention whereby the cutting element 96 is arranged to sever the upper margin of the tape being advanced through the exit slot.

Figure 8:
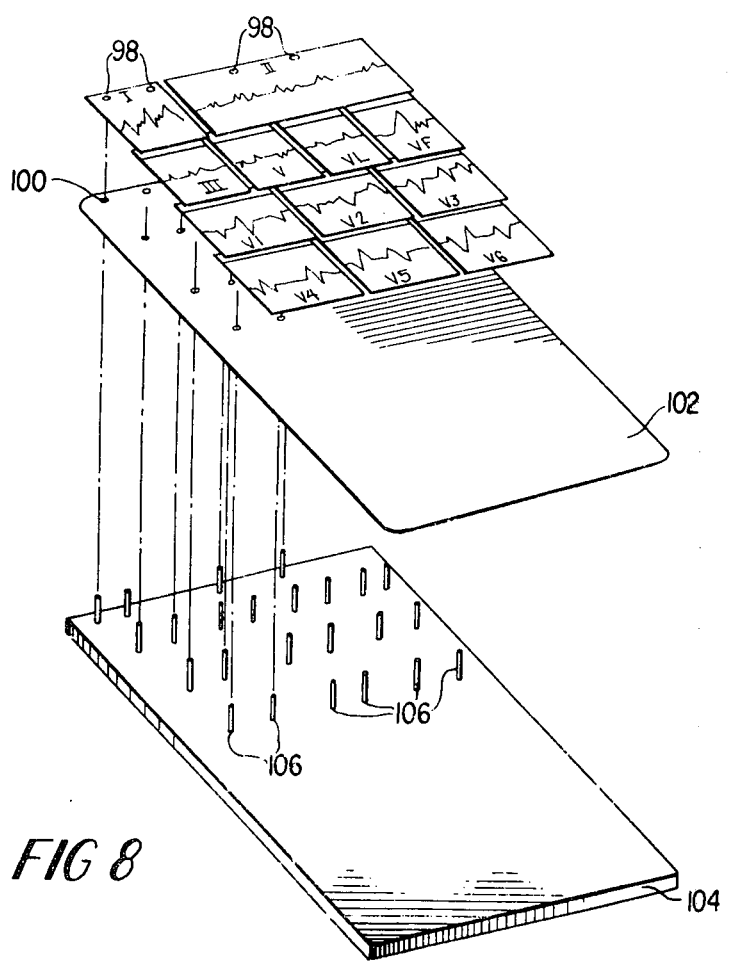
FIG. 8 is an exploded perspective view of an alignment base including a plurality of upstanding pegs to be received in apertures formed in a mounting chart and lead segments to form a composite electrocardiogram display.

FIG. 8 illustrates a method and apparatus for mounting standard ECG lead segments on a prepunched chart (8½ by 11 inches) wherein each segment has been cut in accordance with the following table from standard ECG tape having a total width of 2½ inches and a upper margin of ½ inch.

| TABLE OF LEAD SEGMENT LENGTHS | |
|---|---|
| LEAD SEGMENTS | LENGTH |
| I, III, aVR, aVL and aVF | 2 inches |
| $V_1$ through $V_6$ | 2½ inches |
| II | 6 inches |

Each lead segment is provided with punched apertures 98 corresponding to prepunched apertures 100 in a standardized chart 102 (8½ by 11 inches). Chart 102 may be received on an alignment base 104 having a plurality of upstanding pegs 106 adapted to be received in the prepunched apertures 100 of mounting chart 102 and apertures 98 in the lead segments. The pegs 106 and apertures 100 are arranged to permit the lead segments cut in the lengths listed in the above table to be positioned within the smallest allowable area which at the same time permits maximum display of the information contained thereon. That is to say the pegs are arranged to receive and space the lead segments in four laterally extending rows with lead segments I and II being arranged in end abutting relationship in one row, segments III, aVR, aVL, and aVF being arranged in end abutting relationship in a second row and segments $V_1$ through $V_6$ being arranged in end abutting relationship in the remaining pair of rows. As can be seen in FIG. 8, the pegs 106 and apertures 100 are positioned to cause the upper margins of the lead segments in each of the lower three rows to be overlapped by the next higher row of segments whereby the information contained in these segments may be fully displayed on a single mounting chart within an area of 8½ by 8½ inches. By cutting the lead segments to the prescribed dimensions and by overlapping the upper margin containing non-recorded data in the ordinary ECG tape, the maximum amount of information may be displayed in the minimum amount of space on a standard hospital chart ordinarily 8½ by 11 inches. When using the peg board, the bottom row of segments should be mounted first. The lead segment lengths fully comply with the requirement that sufficient length be allowed for the full display of the electrocardiographic information and at least one of the leads, i.e., lead II, is sufficiently long to permit identification of the auricular complex and to accurately determine the pulse rate. The peg board mounting system may also be used with segments from which the upper margin has been removed by punching alignment holes in the remaining portion of the segment.

It should be understood, however, that the disclosed method for forming a complete electrocardiograph display from unedited standard ECG tape (2½ inches wide having a ½ inch upper margin) does not require the use of a peg alignment base 104 but may rely merely upon a standardized ECG display chart which includes alignment lines indicating the appropriate areas for mounting of each respective lead segment. Accordingly, the critical features of the method in accordance with this invention are the steps of selecting and severing lead segments from an unedited tape of standard width having lengths in accordance with the above table and the step of arranging the lead segments in four laterally extending rows in end abutting relationship in accordance with the grouping illustrated in FIG. 8. By these steps, the area occupied by the upper margin of the lead segments in each of the lower three rows of segments is covered by the next higher row of segments. Accordingly, the upper margins may be overlaped by other lead segments or the margins may be removed prior to mounting on a standardized chart by means of a cutting apparatus such as disclosed in FIG. 7.

A method and apparatus has been disclosed for editing tape containing prerecorded visual information by selecting and removing segments each of which has one of a plurality of predetermined lengths corresponding to the particular type of information contained on the segments. The disclosed apparatus is extremely simple in design yet is readily adapted to different sized tape and to formation of varying sized tape segments. The apparatus is also well suited to permit arrangement of segments on a mounting chart in a minimum amount of space. Accordingly, the method and apparatus is particularly well suited to editing and mounting of ECG tapes in a manner providing for a maximum display of information within a minimum amount of space.

I claim:

1. Apparatus for mounting of segments of tape having information of significance thereon, of a nature such as ECG tapes and the like, in a manner providing for a maximum correlated display for interpretation of such significant information within a minimum amount of space on a single standardized mounting chart, and wherein the tape segments are selected and severed from an unedited tape of standard width, and having lengths in accordance with a predetermined set of prescribed dimensions, and with margins of said tape segments being free from significantly informational recorded data to be interpreted, with the tape segments being each respectively of sufficient length to allow collectively for the full display of the information to be displayed for interpretation, and with at least one of the segment lengths being sufficiently long to permit identification of a particular identifying characteristic of the information to be displayed, the apparatus including a standardized base display chart for the type of information to be displayed and including multiple segment alignment and positional placement means, indicating appropriate areas for positional mounting of each respective tape segment with the information thereon, said segment alignment and placement means being used for facilitating arranging the segments in a plurality of successive laterally extending rows in segment end abutting relationship in accordance with a predetermined grouping arrangement, with the data free area of the margin of tape segments in each of the lower succeeding rows of segments being operatively visually negated in the arranged segments as mounted on the standardized chart.

2. Apparatus as claimed in claim 1 wherein said alignment and positional placement means include a plurality of predeterminedly positionally mounted pegs, and said segments having apertures similarly predeterminedly positionally arranged in said segments for appropriate coaction with and mounting of said segments on said pegs in the appropriate predetermined display.

3. Apparatus as claimed in claim 1, wherein the displayed information consists of a complete electrocardiogram display for a single patient on a mounting chart having pre-punched alignment holes for ECG lead segments selectively edited from ECG tape having an upper margin free of significant information, each lead segment having at least one pre-punched alignment hole in said upper margin, said apparatus including
   a. a base having an upper planar surface for receiving the mounting chart, and
   b. means for positioning the mounting chart on the upper planar surface of the base and for positioning the lead segments on the chart so that all of the information recorded on the lead segments will be visible when attached to the chart as positioned thereon, said positioning means including a plurality of upstanding projections connected with said base, said projections being arranged to pass through the chart and to receive and space the lead segments in a plurality of lateral rows of end abutting lead segments, said projections further being arranged so that the upper margin of each row of lead segments except the upper row is covered by the next above row of lead segments, said lead segments being formed from standard ECG tape 2½ inches wide with a ½ inch upper margin, said projections being arranged in four lateral rows on said base, said rows of projections being spaced 2 inches apart whereby the upper margins of the lead segments in each row except the uppermost row are covered by the next higher row of lead segments, a first group of lead segments each of which is 2 inches in longitudinal length containing information from leads I, III, aVR, aVL, and aVF respectively, a second group of lead segments each of which is 2½ inches in longitudinal length containing information from leads $V_1$ through $V_6$, respectively, and a lead segment 6 inches in longitudinal length containing information from lead II, said projections being so arranged as to position;
  a. four lead segments from the first group in end abutting relationship on the mount to form a first row of lead segments,
  b. lead segments containing lead II information and the remaining lead segment from group one in end abutting relationship on the mount to form a second row of lead segments, and
  c. lead segments from the second group in end abutting relationship to form third and fourth rows of lead segments on the mount.

4. Apparatus as defined in claim 1, including a base and having an upper planar surface for receiving the mounting chart, said positioning means includes a first row of upstanding projections connected with said base and arranged to pass through the mounting chart and through a first group of information bearing segments having information bearing areas of varying length dimension but equal width, said first row of upstanding projections being arranged to position the first group of information bearing segments in a lateral end abutting row on the mounting chart, and a second row of upstanding projections connected with said base and arranged to pass through the mounting chart and through a second group of information bearing segments, said second row of upstanding projections being arranged to position the second group of information bearing segments in a lateral end abutting row spaced from the first group of information bearing segments so that the information free areas of the second group of information bearing segments are covered by the first group of information bearing segments.

5. Apparatus as defined in claim 4, wherein the information bearing segments are standard ECG tape segments 2½ inches wide with a ½ inch upper margin and wherein said positioning means include first, second, third and fourth rows of upstanding projections attached to and arranged laterally across said base, said rows of projections being spaced 2 inches apart to cause the information free areas of the tape segments mounted on the lower three rows of projection to be overlapped by the information bearing areas of the tape segments mounted on the upper three rows, respectively.

6. Apparatus for mounting of segments of tape having information of significance thereon, of a nature such as ECG tapes and the like, in a manner providing for a maximum correlated display for interpretation of such significant information with a minimum amount of space on a single standardized mounting chart, and wherein the tape segments are selected and severed from an unedited tape of standard width, and having lengths in accordance with a predetermined set of prescribed dimensions, and with the upper margins of said tape segments being free from significantly informational recorded data to be interpreted, with the tape segments being each respectively of sufficient length to allow collectively for the full display of the information to be displayed for interpretation, and with at least one of the segment lengths being sufficiently long to permit identification of a particular identifying characteristic of the information to be displayed, the apparatus including a standardized base display chart for the type of information to be displayed and including multiple segment and positional placement means, indicating appropriate areas for positional mounting of each respective tape segment with the information thereon, said segment alignment and placement means being used for facilitating arranging the segments in a plurality of successive laterally extending rows in segment end abutting relationship in accordance with a predetermined grouping arrangement, with the data free area of the upper margin of tape segments in each of the lower succeeding rows of segments covered by a next higher row of tape segments by overlapping the upper margins with other tape segments.

7. Apparatus for mounting of segments of tape having information of significance thereon, of a nature such as ECG tapes and the like, in a manner providing for a maximum correlated display for interpretation of such significant information within a minimum amount of space on a single standardized mounting chart, and wherein the tape segments are selected and severed from an unedited tape of standard width, and having lengths in accordance with a predetermined set of prescribed dimensions, and with the upper margins of said tape segments being free from significantly informational recorded data to be interpreted, with the tape segments being each respectively of sufficient length to allow collectively for the full display of the information to be displayed for interpretation, and with at least one of the segment lengths being sufficiently long to permit identification of a particular identifying characteristic of the information to be displayed, the apparatus including a standardized base display chart for the type of information to be displayed and including multiple segment alignment and positional placement means, indicating appropriate areas for positional mounting of each respective tape segment with the information thereon, said segment alignment and placement means being used for facilitating arranging the segments in a plurality of successive laterally extending rows in segment end abutting relationship in accordance with a predetermined grouping arrangment, with the data free area of the upper margin of tape segments in each of the lower succeeding rows of segments being operatively visually negated by removing these margins prior to mounting on a standardized chart.

* * * * *

UNITED STATES PATENT OFFICE
CERTIFICATE OF CORRECTION

PATENT NO. : 3,959,905
DATED : June 1, 1976
INVENTOR(S) : Arthur K. Thatcher

It is certified that error appears in the above-identified patent and that said Letters Patent are hereby corrected as shown below:

Page 1, under "Related U.S. Application Data" delete --Division of Ser. No. 462,500, April 4, 1974, which is a division of Ser. No. 348,749, April 6, 1973, abandoned-- and add --Division of Ser. No. 462,500, April 4, 1974, now Patent No. 3,875,931, which is a division of Ser. No. 348,749, April 6, 1973, now Patent No. 3,817,137--.

Column 1, line 6, after "April 4, 1974" add --, now Patent No. 3,875,931,--.

Column 1, line 7, after "April 6, 1973, now" delete --abandoned-- and add --Patent No. 3,817,137--.

Signed and Sealed this

Seventeenth Day of August 1976

[SEAL]

Attest:

RUTH C. MASON
Attesting Officer

C. MARSHALL DANN
Commissioner of Patents and Trademarks